United States Patent [19]

Ftaiha

[11] Patent Number: 5,261,612
[45] Date of Patent: Nov. 16, 1993

[54] METHOD AND APPARATUS FOR EXTRACTING INJECTABLE COLLAGEN FROM ADIPOSE TISSUE

[75] Inventor: Zaki Ftaiha, Gladwyne, Pa.

[73] Assignee: Newman-Ftaiha, Inc., Philadelphia, Pa.

[21] Appl. No.: 773,469

[22] Filed: Oct. 9, 1991

[51] Int. Cl.⁵ .......................................... B02C 23/36
[52] U.S. Cl. .......................................... 241/2; 241/20; 241/21; 241/24; 241/62; 241/46.02; 241/46.06; 241/81; 241/199.12
[58] Field of Search ................... 241/2, 24, 79, 301, 241/21, 20, 62, 81, 199.12, 46.02, 46.06; 530/356

[56] References Cited

U.S. PATENT DOCUMENTS

| | | | |
|---|---|---|---|
| 2,920,000 | 1/1960 | Hochstadt et al. | 530/356 |
| 2,934,446 | 4/1960 | Highberger et al. | 530/356 |
| 3,122,081 | 11/1963 | Filz | 241/301 |
| 5,116,389 | 5/1992 | Mitz | 8/127.5 |

*Primary Examiner*—Mark Rosenbaum
*Assistant Examiner*—John M. Husar
*Attorney, Agent, or Firm*—Seidel, Gonda, Lavorgna & Monaco

[57] ABSTRACT

A method and apparatus for extracting injectable collagen from human adipose tissue, such as removed by liposuction procedures. The apparatus includes a clear container with inlet and outlet fittings to be attached to the suction line of a liposuction machine to collect globules of adipose tissue. The container has a needle-like rod disposed in its center and an electric motor and belt drive to rotate the rod at a speed sufficient to cause interstitial reticular fiber from adipose tissue to adhere to and wrap around the rod. Water may then be flowed in through the inlet fitting and drawn out through the outlet fitting to flush the adipose tissue out of container, leaving the reticular fibers on the rod. The rod is then retracted (lowered) through a sleeve which has a rotating chopping blade, scrapping the fiber into a cup area of chopping blades. A pharmaceutical carrier such as saline solution is injected into the container. The rotating chopping blades are driven by the motor and belt to emulsify the reticular fibers into the saline solution. The emulsion is then extracted for use as injectable collagen.

10 Claims, 3 Drawing Sheets

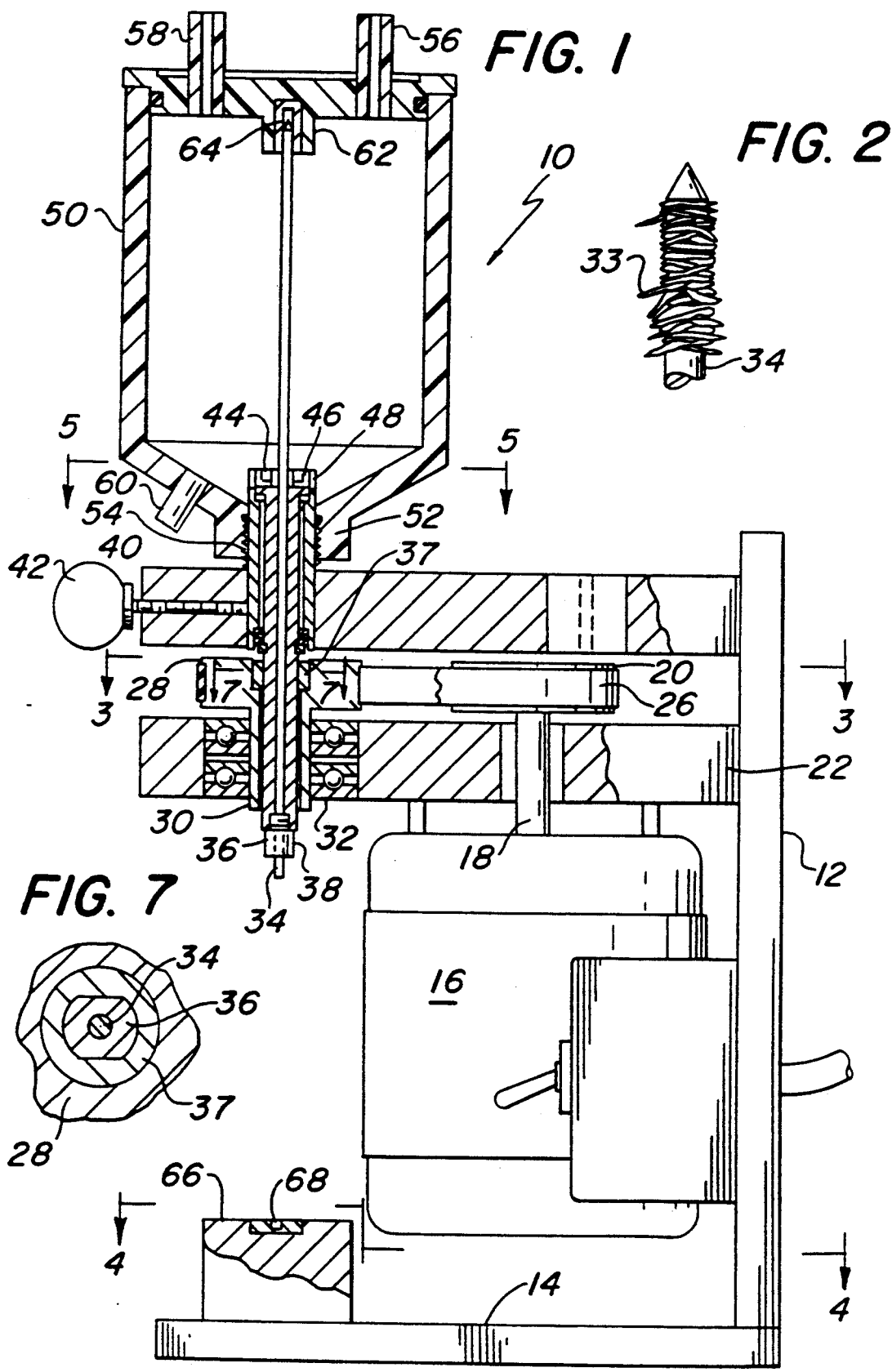

METHOD AND APPARATUS FOR EXTRACTING INJECTABLE COLLAGEN FROM ADIPOSE TISSUE

TECHNICAL FIELD

This invention is related to the general fields of cosmetic and reconstructive surgery, including liposuction procedures and injectable collagen treatments, and to methods of synthesizing injectable collagen. It is specifically related to methods and apparatus for extracting injectable collagen from human adipose tissue removed by liposuction.

BACKGROUND ART

Collagen is the collective term for a group of insoluble fibrous proteins. It is the chief constituent of the fibrils of connective tissue, hide, and tendons. Historically, it has been a source of primitive glue and gelatin extracted from animal parts by prolonged boiling.

Collagen is also a natural polymer. Injectable collagens are various types of liquid emulsion in which collagen is emulsified in a pharmaceutical carrier, such as a saline solution, which can be injected into a patient for soft tissue augmentation. Since it is a bio-material that is usually accepted by the patient's immune system with little or mild host reaction, it is generally preferred over inorganic augmentation material, such as injectable silicone (polydimethylsiloxane).

Commercially available injectable collagen which has been approved for medical use has been predominantly produced from bovine tissue. An example is Zyderm Collagen Implant (ZCI) and Zyplast Collagen Implant (ZI) produced by Collagen Corporation of Palo Alto, California, using collagen extracted from cow skin as the base material.

Despite its superiority to injectable silicone, bovine and other animal-source collagen is still identified as a foreign substance by the human host immune system. Although the immunological reaction is mild in most subjects, producing only short-duration symptoms of local inflammation, a significant percentage of the population will exhibit a more severe reaction. This risk mandates a skin patch test prior to approval for treatment with injectable collagen. The test typically comprises injecting a small quantity of the particular bovine collagen product under the skin of the forearm, and assessing the inflammation response over a period of approximately four weeks. Further, subjects having a history of autoimmune disease are precluded from receiving injectable collagen treatment.

In addition to the risk of allergic reaction, bovine collagen does not exhibit long-term residence at the injection site, and thus requires periodic touch-up injections. It is believed that the reason for dispersion of the bovine collagen is that the fibroblast cells are destroyed when the collagen is extracted from the hides by pepsin digestion and filtration. The absence of linking tissue allows the collagen to be absorbed by the host and not replaced in equal volume at the site by the subject's natural collagen.

Human collagen has heretofore been rarely used except in laboratory testing and experimental procedures, and has typically come from cadavers.

The present inventor and his colleagues proposed at the Sixth Annual Scientific Meeting of the American Academy of Cosmetic Surgery on Jan. 12-14, 1990, that collagen could be derived from a patient's own adipose tissue extracted by liposuction procedures, and processed into an injectable form for immediate use or stored for future use. The reticular fiber connecting adipose tissue is known to be constituted mainly of collagen. Such material, being of patient's own tissue and retaining its fibrous composition, would not trigger an immunological reaction nor dispersion from the injection site. The inventor has now developed a method and apparatus for accomplishing this objective.

SUMMARY DISCLOSURE OF THE INVENTION

The present invention includes a method of extracting injectable collagen from human adipose tissue. Globules of human adipose tissue, such as removed by liposuction procedures, are collected in a container, which in the described apparatus is preferably a disposable container having inlet and outlet fittings adapted to be attached to the suction line of a liposuction device. The interstitial reticular fiber is isolated from the adipose tissue by spinning a needle-like rod in the adipose tissue, with the result that reticular fiber wraps around and adheres to the rod. The adipose tissue is then removed by flushing the container with water and sucking the tissue out through the outlet fitting, while the reticular fibers remain wrapped on the rod inside the container. A pharmaceutical carrier, such as saline solution, is introduced into the container, and the rod is retracted through a sleeve which scraps the fibers into a shallow cylindrical cup. The walls of the cup are defined by rotating chopping blades which chop the reticular fiber sufficiently fine to emulsify it in the saline solution. The emulsion is then removed from the container, preferably into a syringe, for immediate use as injectable collagen suitable for soft tissue augmentation, or extracted and stored for future use or further processing.

An apparatus for carrying out the above method comprises a container with inlet and outlet fittings which may be attached to a liposuction machine to collect globules of adipose tissue. The container has a needle-like rod disposed in its center such that the rod is surrounded by the adipose tissue, and an electric motor and belt drive to rotate the rod at a speed sufficient to cause interstitial reticular fiber from adipose tissue to adhere to and wrap around the needle. Water may then be flowed in through the inlet fitting and drawn out through the outlet fitting to flush the adipose tissue out of container, leaving the reticular fibers on the rod.

The rod is then retracted (lowered) through a sleeve which has a cup area, causing the fiber to be scrapped off the needle into the cup. A syringe fitting is provided to introduce a pharmaceutical carrier such as saline solution into the container. The side of the cup is defined in part by a cylindrical rotating chopping blade, which is driven by the motor and belt to chop and blend the reticular fibers sufficiently fine to emulsify the reticular tissue in the saline solution. The emulsion is then extracted for use as injectable collagen.

BRIEF DESCRIPTION OF THE DRAWINGS

For the purpose of illustrating the invention, the drawings show a form which is presently preferred; it being understood, however, that this invention is not limited to the precise arrangements and instrumentalities shown.

FIG. 1 is a side view in partial section of an apparatus according to the invention.

FIG. 2 is a schematic representation of interstitial reticular fibers wrapped around the rod identified as item 34 of FIG. 1.

FIG. 7 is a top section view of the portion of the apparatus below the line 7—7 of FIG. 1.

BEST MODE FOR CARRYING OUT THE INVENTION

Apparatus

Figure 3:
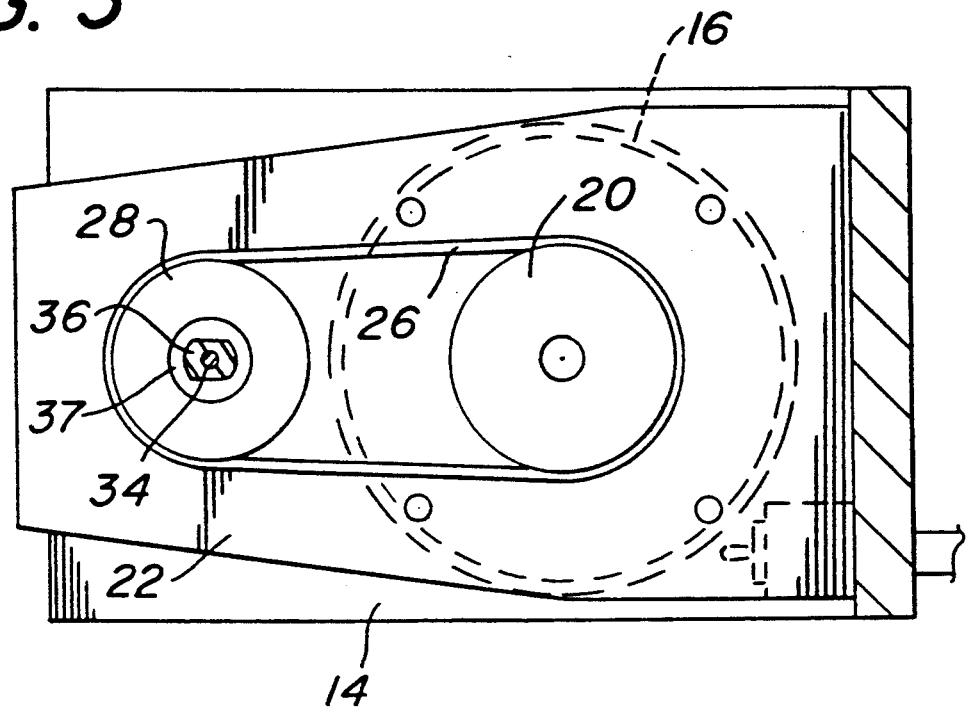
FIG. 3 is a top view of the portion of the apparatus below the line 3—3 of FIG. 1.
Figure 4:
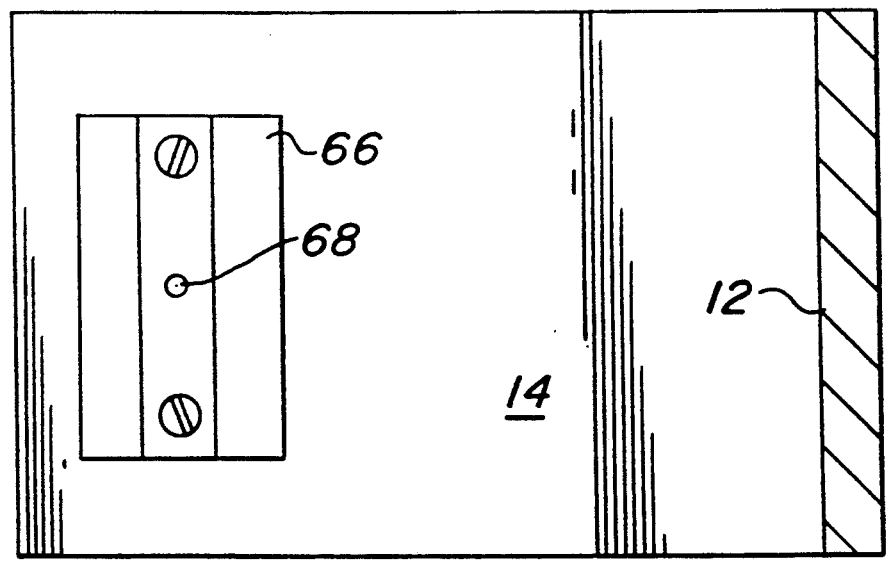
FIG. 4 is a top view of the portion of the apparatus below the line 4—4 of FIG. 1.
Figure 8:
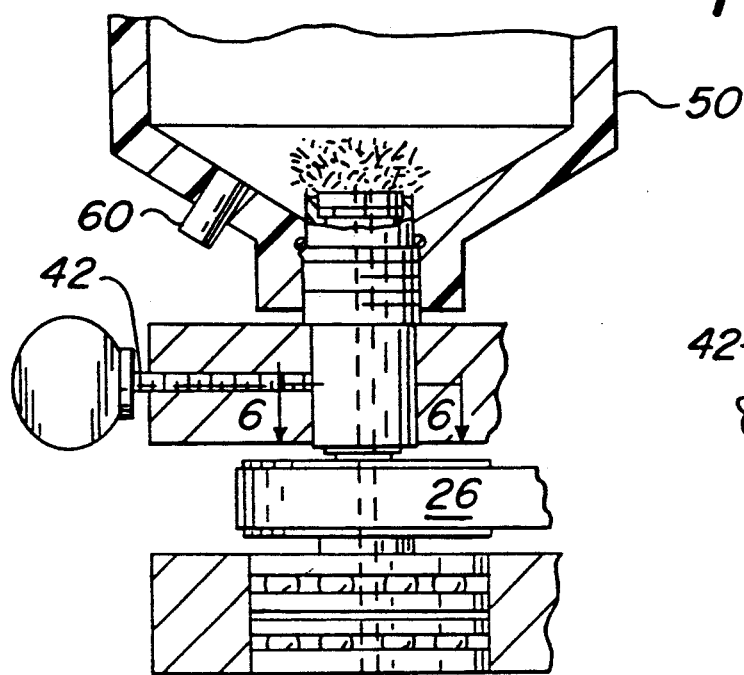
FIG. 8 is a sectional of a portion of the apparatus below the line 8—8 of FIG. 1, with the rod retracted into its support post designated item 66 in FIG. 1.
Figure 6:
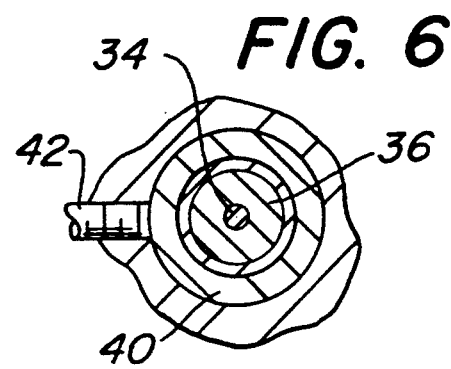
FIG. 6 is a top section view of the portion of the apparatus below the line 6—6 of FIG. 8.

An apparatus (10) for extracting injectable collagen from human adipose tissue is depicted in partial section in FIG. 1. The depicted apparatus illustrates a prototype model built to test the invention, and is thus a compromise between the anticipated best mode and the inventor's need to allow repeated disassembly and adjustment for testing. Consequently, where the anticipated best mode differs from the drawings, both the depicted device and the anticipated best mode will be explained in the text.

The prototype apparatus (10) has a vertical frame post (12) rising from a flat base (14), both members having been fabricated from aluminum stock. A small a.c. electric motor (16) is mounted on the base and controlled by an ON/OFF switch receiving electrical power from conduit through the frame post. In the anticipated best mode, the shape and type of frame is immaterial except insofar as needed to support the items described hereafter, and will likely include a non-conducting cover surrounding the motor and electrical components. The motor type is likewise not critical, but since no significant load will be placed on the motor, it is expected that an a.c. motor using standard 60 cycle domestic current will be preferred.

The motor (16) provides rotational power through a drive shaft (18) to a belt-drive rotor (20). The shaft (18) extends through a journal bearing in a lower support arm (22). The rotor (20) lies between the lower support arm and an upper support arm (24), and drives a belt (26) which rotates a work rotor (28). The rotor shaft (30) of the work rotor extends through a roller-type bearing (32) in the lower support arm (22). The ratio of drive rotor to work rotor diameters can be selected according to the motor speed to impart a rotation of approximately 25,000 r.p.m. to the work rotor.

The purpose of the motor and drive components is to power a needle-like member and chopping blades in a container. As shown in FIG. 1, the needle member is a thin cylindrical rod (34) inside a rotating sleeve (36). The sleeve is coupled to the work rotor by a resilient bushing (37) which causes the sleeve to rotate with the rotor, but allows clutching slippage if sleeve rotation becomes impeded. The rod is inserted into, and can move up and down within, a hollow center bore of the sleeve, but may be locked in place at the full UP position, as depicted in FIG. 1, by a cap fitting (38). The cap fitting is fixed to the rod and has a short thread to engage a threaded mouth of the sleeve. It will be apparent from the drawings that when the rod (34) is locked with the rotating sleeve (36), it rotates with the sleeve and work rotor.

A non-rotating post (40) passes through a bore in the upper support arm (24) and encloses the sleeve (36). Small washers may be used as a bearing seal between the post and sleeve. A screw (42) is used to secure the post (40) in the upper support arm. The post (40), sleeve (36) and rod (34) can be removed from the top when the screw (42) is loosened.

Figure 5:
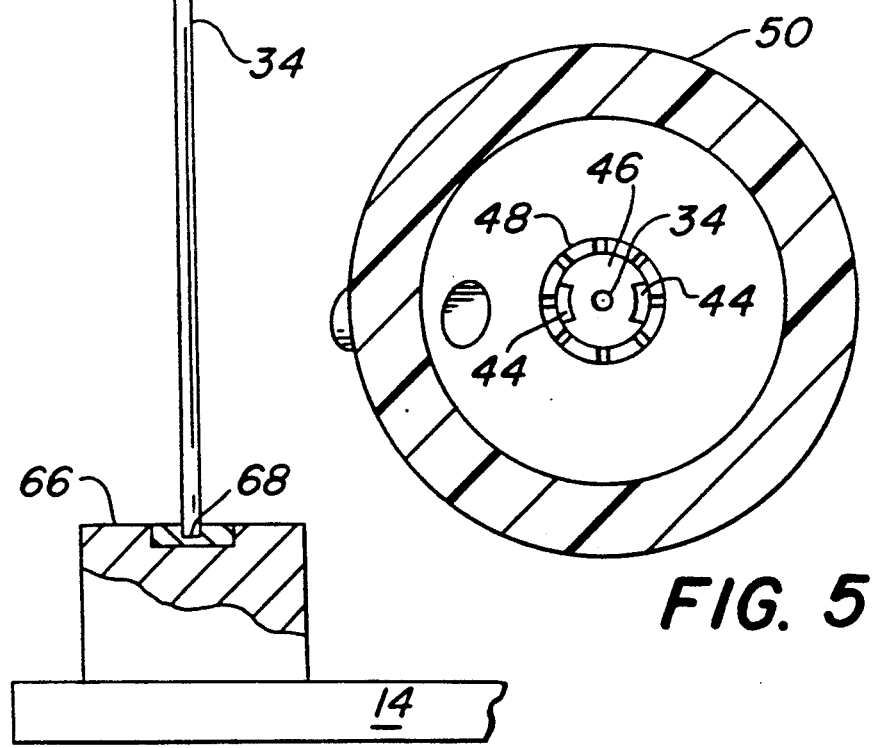
FIG. 5 is a top section view of the portion of the apparatus below the line 5—5 of FIG. 1.

The sleeve (36) has a chopping blade rotor (44), in the form of two opposed blades, on its upper face. The post (40) has a cylindrical cup area (46), in which the sides of the post above the sleeve (36) are disposed in eight equal segments, with a slot opening between segments to create a chopping blade stator (48), as shown in FIG. 5. The rotor (44) and stator (48) combine to create a chopping blade mechanism for chopping and blending the reticular fibers sufficiently fine to emulsify the reticular tissue in a saline solution.

A clear open-mouthed container (50) is provided for collecting globules of human adipose tissue, such as the tissue removed by liposuction procedures, which in the anticipated best mode is preferably an integrally-formed disposable container of glass or clear plastic. In the depicted prototype, the container has a removable cap to facilitate washing for repeated use and for ease of fabrication. The container (50) has a threaded mouth (52) to engage mating threads (54) on the post (40) by which the container can be mounted over the post and closed to the outside environment.

At the top of the container are an inlet fitting (56) and an outlet fitting (58), both adapted to be attached to the pneumatic suction line of a liposuction device. It will be apparent that globules of adipose tissue drawn from the patient through a suction probe attached to the line will enter at the inlet fitting and be collected in the container. A syringe fitting (60) extends out of a lower side of the container near the lowest point to permit introduction of saline solution and extraction of collagen emulsion by syringe. As known in the art, a syringe fitting may be plugged with any suitable impermeable material, such as resilient foam, through which a syringe may be inserted and withdrawn without creating a permanent hole.

At the inside top of the container is a post (62) having a bearing (64) to support the upper end of the needle when it is rotated. A post (66) also arises from the base (14) and has a bore (68) to receive and hold the base of the needle when it is pulled through the sleeve. The post and bore serve as a down-stop limit such that when the needle is lowered to the bottom of the bore, the needle tip is essentially flush with the base of the cup section (46) inside the container.

Operation

The apparatus (10) may be used to extract injectable collagen from human adipose tissue as follows. The apparatus (10) is placed in the pneumatic suction line of a liposuction device line, such that the inlet fitting (56) is attached to the portion of the line leading to the probe and the outlet fitting (58) is attached to the line leading to the suction source. Globules of human adipose tissue are thus collected in the container (50). The rod (34) is raised inside the container with its tip end fully inside the bearing (64) and locked in place by the threaded cap fitting (38) while the adipose tissue is being collected. The adipose tissue surrounds the centrally-placed rod.

After the adipose tissue is collected, the rotor (28) is driven by the motor and belt to rotate the rod at approximately 25,000 r.p.m. in the adipose tissue. The interstitial reticular fiber of the globules wrap around and adhere to the spinning rod, as shown in FIG. 2.

The container is then flushed with water entering the inlet fitting and sucked out the outlet fitting to remove the adipose tissue, while the reticular fibers wrapped on the rod remain inside the container. A syringe of pharmaceutical carrier, such as saline solution, is then introduced into the container through the syringe fitting (60).

The rod is then unlocked from the sleeve by turning the threaded cap-fitting (38), and lowered into the post (66). The bore (68) receives the base of the rod and serves as a down-stop limit such that the rod's tip is essentially flush with the base of the cup section (46) inside the container. As the rod is lowered, the reticular fiber is scrapped off into the cup (46).

While the rod is being retracted to scrap the fiber into the cup, the motor may be again started to rotate the sleeve and its chopping rotor (44), which in conjunction with the stator (48), act as blades which chop the reticular fibers sufficiently fine to emulsify them in the saline solution, and blend the chopped fiber into the saline as an emulsion. The emulsion is then extracted by syringe from the fitting (60).

The emulsion extracted into the syringe is suitable for immediate use as injectable collagen suitable for soft tissue augmentation. Alternatively, it can be extracted from the syringe and stored for future use or further processing.

Industrial Applicability

It is expected that the apparatus will be used by cosmetic and reconstructive medical professionals and institutions to obtain collagen from patients to be used in soft tissue augmentation or other procedures.

The present invention may be embodied in other specific forms without departing from the spirit or essential attributes thereof and, accordingly, reference should be made to the appended claims, rather than to the foregoing specification, as indicating the scope of the invention.

I claim:

1. A method of extracting injectable collagen from human adipose tissue, comprising the steps of:
   (a) collecting globules of human adipose tissue in a container;
   (b) isolating interstitial reticular fiber tissue from the adipose tissue;
   (c) removing the adipose tissue from the container while retaining the isolated reticular fiber tissue inside the container;
   (d) introducing a pharmaceutical carrier liquid into the container;
   (e) chopping the reticular fibers sufficiently fine to emulsify the fiber tissue in the carrier;
   (g) removing the emulsion from the container for use as injectable collagen.

2. A method as in claim 1, further comprising: collecting the adipose tissue from a suction line of a liposuction device.

3. A method as in claim 1, further comprising isolating interstitial reticular fiber tissue from the globules of adipose tissue by spinning a needle-like member in the adipose tissue such that reticular fiber tissue adheres to the member.

4. A method as in claim 1, further comprising: removing the adipose tissue from the container while retaining the isolated reticular fiber inside the container by flushing the adipose tissue out of the container with water.

5. An apparatus for extracting injectable collagen from human adipose tissue, comprising:
   a container for collecting globules of human adipose tissue;
   means for isolating reticular fibers from the adipose tissue inside the container;
   means for removing the adipose tissue from the container while retaining the isolated reticular fiber inside the container;
   means for introducing a pharmaceutical carrier liquid into the container;
   a cutting and blending device for reducing the reticular fibers sufficiently fine to emulsify the reticular tissue in the carrier; and
   means for extracting the emulsion for use as injectable collagen.

6. An apparatus as in claim 5, wherein the means for isolating reticular fibers from the adipose tissue inside the container comprises:
   a needle-like rod disposed within the container to be surrounded by adipose tissue; and
   means for rotating the rod at a speed sufficient to isolate interstitial reticular fiber from the globules of adipose tissue.

7. An apparatus as in claim 5, wherein the container is placed in the suction line of a liposuction device between a suction probe and a suction source, to collect globules of adipose tissue removed from a human patient by the suction probe.

8. An apparatus as in claim 7, wherein the means for isolating reticular fibers from the adipose tissue inside the container comprises:
   a needle-like rod disposed within the container to be surrounded by adipose tissue; and
   means for rotating the rod at a speed sufficient to isolate interstitial reticular fiber from the globules of adipose tissue.

9. An apparatus as in claim 7, wherein the container is a vessel of optically clear material having inlet and outlet fittings for connection to the suction line of a liposuction device.

10. An apparatus for extracting injectable collagen from human adipose tissue, comprising:
   a support structure for supporting a needle-like rod in a vertical orientation with freedom of movement in the vertical direction and rotational freedom around the rod's long axis;
   an open-mouthed container placed in the suction line of a liposuction device between a suction probe and the suction source, and to collect globules of adipose tissue removed from a human patient by the suction probe;
   means for attaching the container to the support structure such that when the container is attached to the structure, the mouth of the container is closed by the structure and the rod is aligned to move vertically into the container;
   means for moving the rod vertically into the container;
   means for rotating the rod at a speed sufficient to cause interstitial reticular fiber from the globules of adipose tissue to adhere to and wrap around the rod;

a cutting and blending device comprising rotating blades surrounding the rod within the container;

means for lowering the rod vertically through the cutting device to scrape reticular fiber from the rod into the cutting and blending device;

means for introducing a pharmaceutical carrier liquid into the container;

means for rotating the blades of the cutting and blending device to emulsify the reticular fibers into the carrier; and means to remove the emulsion from the carrier as an injectable collagen.

* * * * *